United States Patent [19]

Sekura

[11] Patent Number: 4,762,710
[45] Date of Patent: Aug. 9, 1988

[54] NOVEL METHOD OF PREPARING TOXOID BY OXIDATION AND METAL IONS

[75] Inventor: Ronald D. Sekura, Rockville, Md.

[73] Assignee: The United States of America as represented by the Department of Health and Human Services, Washington, D.C.

[21] Appl. No.: 874,637

[22] Filed: Jun. 16, 1986

[51] Int. Cl.$^4$ .................... A61K 39/10; A61K 39/02; C07K 15/04
[52] U.S. Cl. ........................................ 424/92; 424/88; 530/395; 530/404; 530/405; 530/406; 530/410
[58] Field of Search .................... 424/88, 92; 530/404, 530/405, 406, 410, 395

[56] References Cited

U.S. PATENT DOCUMENTS

| | | | |
|---|---|---|---|
| 3,529,057 | 9/1970 | Tsuchiya et al. | 424/92 |
| 3,825,525 | 7/1974 | Mullan et al. | 530/404 X |
| 3,968,202 | 7/1976 | Stein | 424/92 |
| 4,058,599 | 11/1977 | Bauer et al. | 424/92 |
| 4,172,126 | 10/1979 | Okonogi et al. | |
| 4,185,090 | 1/1980 | McIntire | 424/92 |
| 4,256,732 | 3/1981 | Malley | 530/406 X |
| 4,314,993 | 2/1982 | Wijnendaele | 530/406 X |
| 4,419,444 | 12/1983 | Ouash | 530/395 X |
| 4,479,940 | 10/1984 | Bizzini | 530/404 X |
| 4,578,270 | 3/1986 | Csizer et al. | 424/92 |
| 4,606,919 | 8/1986 | Stojkovic et al. | 424/92 |
| 4,687,738 | 8/1987 | Ginnaga et al. | 424/92 X |

OTHER PUBLICATIONS

Methods in Enzymology, vol.-91, Part 1 (1983), 580-609, Colowick et al.
Biochemistry of the Amino Acids, Meister (1965), 468-473.
Chemical Reactions of Polymers (1966), vol.-XIX, pp. 376-381, Fettes.
Chem. Abstracts, 33, 1939, 7336$^9$, Velluz.
Chem. Abstracts, 51, 1957, 16714h-i, Weil et al.
Chem. Abstracts, 52, 1958, 13858h-i, Miyasaki et al.
"Preparation of Improved Vaccine for Hooping Cough", No. 55-118420, Sankyo.
Sekura, et al., (1983), J. Biol. Chem., 258:23, pp. 14647-14651, "Pertussis Toxin, Affinity Purification of a New ADP-Ribosyltransferase".
Sekura, et al., (1985), Methods of Enzymology, 109, p. 566, "ADP-Ribosylation of Membrane Components by Pertussis and Cholera Toxin".

Primary Examiner—Howard E. Schain
Attorney, Agent, or Firm—Holman & Stern

[57] ABSTRACT

A method of preparing toxoid by treating a toxin with an oxidizing agent is described. Preparation of a vaccine against pertussis in accordance with the method is illustrated.

18 Claims, 3 Drawing Sheets

NOVEL METHOD OF PREPARING TOXOID BY OXIDATION AND METAL IONS

BACKGROUND OF THE INVENTION

1. Technical Field

The present invention is related to preparing toxoid. More particularly, the present invention is related to a novel method for chemical inactivation of toxin, particularly with $H_2O_2$ and preparation of an acellular, detoxified vaccine therefrom.

2. State of the Art

Whooping cough (pertussis) is an infectious disease caused by the organism *Bordetella pertussis*. The incidence of this disease can be effectively controlled by immunization. At present national and world health organizations recommend that infants be immunized to prevent the incidence and spread of pertussis.

Three types of vaccines have been used for immunization against *Bordetella pertussis*. The most widely used vaccine consists of whole *Bordetella pertussis* organisms which are no longer viable. This vaccine, while effective in preventing disease, has several problems associated with it: (1) Administration leads to local erythema, (2) Use has been associated with induction of elevated temperature, general fretfullness and malaise, and (3) In certain instances it has been contended that administration can lead to severe neurologic sequella. In another vaccine, the pertussis component was prepared as a urea extract. This product was in use from about 1969 to 1974 but has now been withdrawn from the market. In Japan a new pertussis vaccine is in use prepared from culture supernatants of *Bordetella pertussis*. This material contains all culture supernatant proteins and because of variabilities in cultivation of the organism final composition can vary. In addition, use of gluteraldehyde or formaldehyde as inactivating agents can sometimes lead to aggregated materials that are subject to reversion to active toxin. It is believed that these aldehydes cause the formation of Schiff bases which are chemically unstable and thus render the toxoids subject to reversion to active toxin. Preparations of other toxins such as tetanus, diptheria and cholera toxins by hitherto known methods suffer from similar drawbacks. Hence, the need for an improved method of preparing safe and stable acellular toxins substantially free of undesirable components and effects is quite apparent.

SUMMARY OF THE INVENTION

It is, therefore, an object of the present invention to prepare a toxoid wherein the toxin has been irreversibly inactivated by chemical means.

It is a further object of the present invention to prepare a pertussis vaccine free of impurities such as endotoxin and other toxic materials which usually cause adverse side effects.

It is a still further object of the present invention to provide a method of protecting a susceptible host against pertussis by administering to said host an immunogenic amount of the antigen prepared in accordance with the present invention.

Other objects and advantages will become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1:
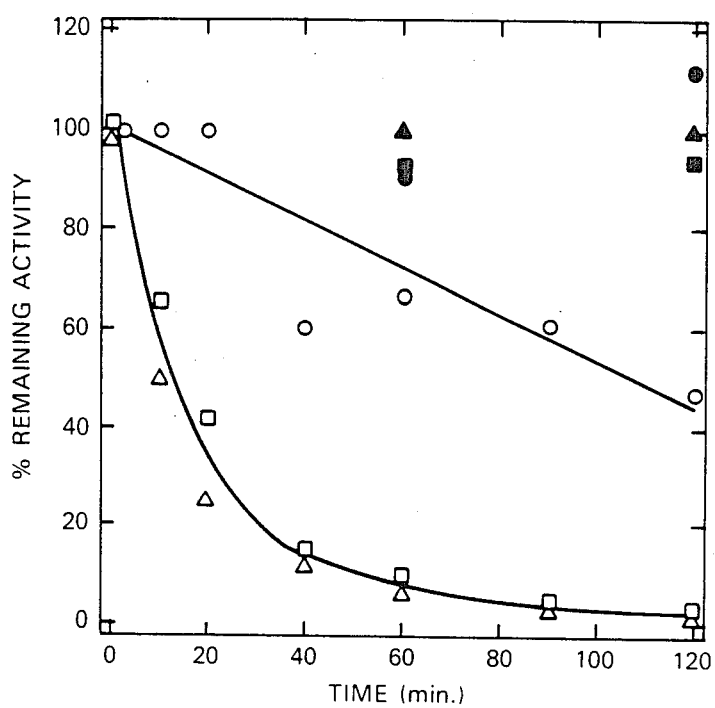
FIG. 1 shows kinetics of hydrogen peroxide inactivation of pertussis toxin.
Figure 2:
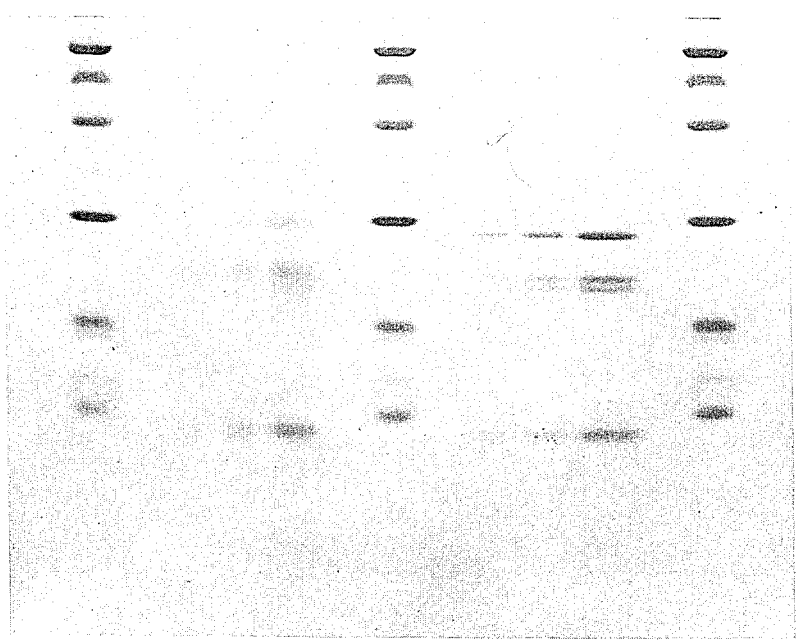
FIG. 2 shows sodium dodecyl sulfate (SDS) polyacrylamide gel electrophoresis (PAGE) of pre-toxoid and PTH-06 toxoid.

The above and other objects and advantages of the present invention are achieved by a method of preparing a toxoid by treating at least partially purified or isolated toxin with an oxidizing agent in an amount sufficient to chemically inactivate said toxin while retaining immunogenic property of said toxin and thereafter recovering the intact toxoid or parts thereof and preparing a vaccine therefrom.

The term "oxidizing agent" as used herein means any agent which will oxidize the toxin at certain specific positions in the peptide chain where such amino acid residues as cysteine, cystine, methionine, tryptophan and/or tyrosine occur. Such oxidants may also be organic or metallic. Preferred examples of such oxidizing agents are hydrogen peroxide, sodium peroxide, N-chloro-4-methylbenzenesulfonamide sodium salt (chloramine-T), performic acid, dioxaneperoxide, periodic acid, Na-permanganate, sodium hypochlorite and the like well known in the art. Among such oxidizing agents $H_2O_2$ is particularly preferred because of its ease of handling, cost factor and ready availability.

Unless specifically defined otherwise, all scientific or technical terms used herein have the same meaning as generally understood by one of ordinary skill in the art to which the invention belongs. All references cited hereunder are incorporated herein by reference. Although any similar or equivalent methods and materials as described herein can be employed for the practice of the invention or for the tests mentioned herein, the preferred methods and materials are now described.

The term "substantially" purified or isolated as used herein means that the toxin has been separated and/or purified at least to a degree that it is free of those particulate or soluble bacterial contaminants or impurities which are likely to cause adverse reaction when the toxoid is administered to a host.

It is noted that the starting material need not be a purified bacterial preparation. Only partially separated or purified preparation may serve just as well for the process described herein. The essential steps of the process except treatment with an oxidizing agent are similar to what has been described by Sekura et al in Journal of Biol. Chem. 258: 14647–14651, 1983 which is incorporated herein by reference and now outlined using pertussis toxin as an illustrative example.

MATERIALS AND METHODS

Materials—Affi-Gel blue (100–200 mesh) as obtained from BioRad, cyanogen bromide-activated Sepharose 4B was purchased from Pharmacia, and fetuin prepared by the Spiro method was obtained from Gibdo. Filamentous hemagglutinin and pertussis toxin from strain Tohama and antibodies to these proteins were prepared as described by Cowell et al., Seminars in Infectious diseases Vol. IV: Bacterial Vaccines, 4: 371–379 (1982). Strains of *B. pertussis* were from the collection maintained at the Pertussis Branch, Office of Biologics, Bethesda, MD. Other materials used in this study were of reagent quality and obtained from common suppliers.

The fetuin affinity resin was prepared by coupling 200 mg of fetuin with 25 g of the cyanogen bromide-activated Sepharose 4B according to the manufacturer's recommended procedure.

Culture of Organisms—Lyophilized cultures of *B. pertussis* (Office of Biologics, strain 165) were opened and passaged twice at 37° C. on Bordet-Gengou blood agar plates. The growth from each of two plates was then used to inoculate starter cultures (200 ml of Stainer-Scholte media (Hewlett et al., J. Bacteriol. 127: 890–898, 1976) in 500 ml flasks) which were incubated overnight, at 37° C., with agitation. Fernback flasks (2.8 liters) containing 1.3 liters of Stainer-Scholte media were inoculated with growth from starter cultures to an initial $A_{650}$ of between 0.05 and 0.1. Bacteria were then cultured at 36° C. on a gyrorotary shaker at 120 rpm for about 40 to 60 h to an $A_{650}$ of between 2.5 and 2.8. Bacteria can, of course, be grown under other conditions well known in the art and the volumes can be adjusted appropriately as desired. In addition, other strains of *B. pertussis* can also be used.

Assay of Pertussis Toxin—Several techniques well known in the art are available for estimation of the toxin. For routine rapid assays used during the course of the purification, the hemagglutinating activity of pertussis toxin was followed using goose red blood cells as described by Irons et al., Biochim. Biophys. Acta 580: 175–185 (1979). Lymphocytosis-promoting activity was assayed as described by Sato et al., Infect. Immun. 6: 899–904 (1972). One unit of lymphocytosis-promoting activity is defined as the amount of material that causes an increase of 10,000 white blood cells/liter above background, 3 days after injection. With highly purified preparations of pertussis toxin, the hemagglutination and lymphocytosis-promoting activities are about 150,000 and 30,000 units per mg, respectively. Toxin was also determined by conventional enzyme-linked imunosorbent assay (ELISA). Purified goat anti-pertussis toxin was used to coat the immobile phase. After reaction with antigen-containing preparations, the immobile phase was reacted with an antibody-alkaline phosphatase adduct and pertussis toxin was estimated by the resultant alkaline phosphatase activity following standard procedures. A similar technique was used to estimate filamentous hemagglutinin.

Other Methods—Electrophoresis in an acid gel system was performed according to the method of Reisfield et al., Nature 195: 281–283 (1962). SDS gel electrophoresis was performed as described by Laemmli, Nat. New Biol. 227: 680–685 (1970). Samples were prepared by SDS-gel electrophoresis by treating 10–50 μg of protein in a final volume of 100 μl with 1% SDS and heated for about 2 min at 100° C. in the presence or absence of 2% β-mercaptoethanol. For two-dimensional electrophoresis nonreduced samples were run first using Laemmli gels. Strips were cut from these gels and soaked for 1 h in running buffer containing 1% β-mecaptoethanol. After washing thoroughly with running buffer, the running gel was cast around the strip and electrophoresis was conducted in the second dimension. Gels were stained with Coomassie blue (Oakley et al., Anal. Biochem. 105: 361–363, 1980). Kodak XAR-2 film was used for autoradiography of $^{32}P$-labeled proteins. Densitometry was performed at 633 nm with a Biomed densitometer.

Amino acid analyses were conducted as described by Oliveira et al., J. Biol. Chem. 254: 489–502 (1979). Carboxymethylcysteine was determined after reaction of reduced and nonreduced samples (prepared as described above for the SDS complexes) with standard iodoacetamide reaction.

Protein was determined by the method of Lowry et al., J. Biol. Chem. 193: 265–275 (1951) using bovine serum albumin as the standard. Since many samples contained materials which interfere with this assay, determinations were made using precipitates obtained after treatment of protein samples with 5% trichloroacetic acid.

Purificaton of Pertussis Toxin—The supernatant from cultures of strain 165 was prepared by centrifugation at 6000×g at 4° C. for 30 min. The supernatant was adjusted to pH 6.0 with HCl, and Affi-Gel blue (10 ml of packed resin per liter of supernatant) was added. The resulting slurry was stirred at 4° C. for 48 h. The resin was allowed to settle for about 2 h and the supernatant solution siphoned off. Subsequent steps of the purification were performed at about 25° C. The resin was then packed into a column (6×7 cm) and eluted at a flow rate of about 250 ml/h with 450 ml of 0.25M sodium phosphate, pH 6.0, 450 ml of 0.05M Tris-HCl, pH 7.4 (Buffer A), and 450; ml of Buffer A containing 0.75M magnesium chloride. Fractions showing activity were pooled, diluted with an equal volume of water and applied to a fetuin-agarose column (2.5×7 cm) and eluted at a flow rate of about 40 ml/h as follows: 40 ml of Buffer A; 40 ml of Buffer A containing 1M sodium chloride; and 40 ml of Buffer A containing 4M magnesium chloride. Fractions containing pertussis toxin were pooled and passed (at 30 ml/h) through a Sephadex G-25 (2.5×35 cm) column equilibrated with Buffer A containing 0.5M sodium chloride. Protein was then precipitated by adding solid ammonium sulfate (0.65 g/ml) and stirring at 4° C. overnight. The precipitate, collected by centrifugation for 30 min at 20,000×g and 4° C., was resuspended in Buffer A to which solid ammonium sulfate (0.65 g/ml) was added. Stored in this buffer at 4° C., the toxin is stable for months.

Pertussis toxin prepared by the above procedure is a single protein composed of non-identical subunits with molecular weight of about 31,000, 26,000, 25,000 and 11,500 as determined by electrophoresis on 15% SDS gels.

HYDROGEN PEROXIDE INACTIVATION OF PERTUSSIS TOXIN

In preparation for reaction with hydrogen peroxide, pertussis toxin prepared as described supra, is transferred into a suitable buffer at protein concentrations of about 0.1 to 0.5 mg/ml. Buffers such as borate, carbonate, Tris, phosphate, perchlorate and the like well known in the art are suitable and the reaction pH can be varied from about 3.5 to 8.5 or greater, it being understood that reaction pH per se is not a critical factor. When inactivation is carried out at the preferred pH of 8.5, the preferred reaction mixture contains 0.1M sodium borate, pH 8.5; 0.001M sodium EDTA, pH 8.5; 0.0001M ferric sulfate or other metal salt such as ferric chloride, ferrous or ferric sulfate and other metal salts such as cobalt chloride, chromium chloride and the like; 1.2% hydrogen peroxide; and up to 10% saturated ammonium sulfate. The reaction rate depends on the concentrations of hydrogen peroxide, ferric sulfate and EDTA. Ferric ion or other trace metal salts or ions such as mentioned herein supra, is essential since inactivation can be blocked or controlled by chelating agents such as EDTA (ethylenediaminetetraacetate). The reaction is generally performed at about 37° C. and the extent of reaction is monitored by assaying pertussis toxin catalyzed ADP-ribosylation of transducin and pertussis toxin mediated agglutination of goose erythrocytes, supra. The time dependence for inactivation with hydrogen peroxide is shown in FIG. 1. In addition, data are presented showing the reactivity of the resultant toxoid as an antigen in an pertussis toxin specific ELISA. Preparations of pertussis toxoid suitable for use as pertussis vaccines are obtained by this method using reaction times of about two hours. The reaction with hydrogen peroxide can be quenched by the addition of EDTA or other chelating agents, or by the addition of catalase, and/or by gel filtration on a medium such as Sephadex G-25 or the like.

CHARACTERIZATION OF PETUSSIS TOXOID

Toxoid preparations prepared by the method described above have been monitored for various biological activities as summarized in Table I and FIG. 1. The terms PTH04, PTH-05 and PTH-06 refer to specific lots that have been prepared. The terms "Toxoid" and "Pre-toxoid" refer to preparations of the toxin before and after treatment with an oxidizing agent, respectively. These data show that treatment of pertussis toxin with hydrogen peroxide results in a preparation which is non-toxic but still has immunologic determinants that cross react with antibodies directed specifically against native toxin, thereby demonstrating potent antigenic quality retained by the $H_2O_2$ treated toxin.

TABLE II-continued

| Selected amino acid composition of PTH-04 and its pre-toxoid | | |
|---|---|---|
| Amino acid | Pre-toxoid | Toxoid |
| Cysteine | 0.13 | <0.06 |
| Methionine | 0.15 | <0.02 |
| Tyrosine | 0.72 | 0.31 |

Amino acid contents are expresssd as molar ratio relative to alanine.
The ninhydrin color values assigned to the cysteic acid and methionine (0) are the averages of values for alanine and methionine.

SDS-gel electrophoresis of hydrogen peroxide inactivated pertussis toxin results in several changes relative to untreated toxin (FIG. 2). There is a shift in the apparent migration of the S1 subunit (Mr=31,000) to a higher molecular weight and the protein band is more diffuse. Resolution of the S2 (Mr=26,000) and S3 (Mr=25,000) subunits is reduced relative to untreated toxin. Traces of stainable material are seen between the 11,000 and 25,000 molecular weight regions. The S4,5 (Mr=11,000) components of toxoid and pertussis toxin are similar. These changes are consistent with chemical modification of the protein by hydrogen peroxide. Without being bound to any theory, it is postulated that the diffuse material observed between the S3 and S4,5 bands is probably the result of limited cleavage of these polypeptides.

PREPARATION OF ADSORBED PERTUSSIS TOXOID

For use as pertussis vaccine, pertussis toxoid is adsorbed to a suitable adjuvant such as aluminum adjuvant. For this purpose Alhydrogel (Superfos Kemi a/s) has been used but other adsorbants such as aluminum phosphate or aluminum hydroxide or salts generated de novo could be equally well employed. Between 20 and 200 μg of pertussis toxoid is adsorbed per mg aluminum, to give a final protein concentration of between 20 and 200 μg per ml. In general adsorption is performed in conventional phosphate buffered saline, ph 7.4, at 4° C. with agitation for 24–48 hr. Immediately prior to adsorption toxoid solutions are sterilized by filtration through a 0.22 micron filter and thimersol (1:10,000; w:v) is added as a preservative. Of course, other adsorbents, adjuvants, preservatives or additives well known in the art could also be employed. In addition pertussis toxoid itself is immunogenic.

TABLE I

Residual biological activities of three lots of pre-toxoid and pertussis toxoid

| Assay system | PTH-04 Pre-toxoid | PTH-04 Toxoid | PTH-05 Pre-toxoid | PTH-05 Toxoid | PTH-06 Pre-toxoid | PTH-06 Toxoid |
|---|---|---|---|---|---|---|
| Protein (μg/ml) | 454 | 220 | 366 | 173 | 256 | 173 |
| HA[a] | 28,000 | <230 | 139,000 | <578 | 50,000 | 462 |
| LPA[b] | 25,000 | <23 | 11,000 | <29 | 5700 | <29 |
| HSA[c] | $1.3 \times 10^{-6}$ | $2.9 \times 10^{-2}$ | $6.7 \times 10^{-6}$ | $>3.5 \times 10^{-2}$ | $6.5 \times 10^{-5}$ | $>3.5 \times 10^{-2}$ |
| TD[d] | ND | $8.6 \times 10^{3}$ | $1.2 \times 10^{6}$ | $4.2 \times 10^{3}$ | $5.8 \times 10^{5}$ | $3.8 \times 10^{3}$ |
| CHO cell (ng/ml)[e] | ND | ND | 0.31 | $>10^{4}$ | 0.31 | $>3.4 \times 10^{3}$ |

[a]Hemagglutination as units/mg protein
[b]Lymphocytosis-promoting activity - units/milligram protein
[c]Histamine sensitizing activity - mg required for $LD_{50}$
[d]ADP-ribosylation of transucin activity expressed as ng active pertussis toxin per mg protein.
[e]Final concentration of protein required to induce clustering of cells.

Amino acid analysis of pertussis toxoid preparations prepared by hydrogen peroxide treatment in the presence of ferric sulfate demonstrates several significant alterations in composition. Treatment with ferric sulfate results in a reduction of cysteine, methionine, and tyrosine, as shown in Table II. Consistent with oxidation of methionine and cysteine residues is the appearance of early eluting amino acid which may correspond to cysteic acid or methionine sulfoxides or sulfones. The nature of the chemical modification achieved by hydrogen peroxide treatment in the presence of trace metal is not readily reversed, and is indicative of the stability of toxoids thus produced against reversion to active toxin.

TABLE II

| Selected amino acid composition of PTH-04 and its pre-toxoid | | |
|---|---|---|
| Amino acid | Pre-toxoid | Toxoid |
| Cysteic acid and methionine (0) | <0.01 | 0.18 |

SEROLOGIC RESPONSE TO PERTUSSIS TOXOIDS

Immunization of mice with adsorbed pertussis toxoids leads to an immune response, as measured by ELISA, which is both dose and time dependent (Table III, FIG. 3). A dose response is seen with pertussis toxoids administered over the range of 3 to 75 μg with the 75 μg dose giving the highest response at both 2 and 4 weeks. The level of antibody produced at all doses of toxoid, is higher at 4 weeks than at 2 weeks post immunization. Measurement of serologic response by monitoring the ability of serum antibodies to neutralize the effect of active pertussis toxin on CHO-cells exhibits similar features (Table IV, FIG. 3). The response is dose and time dependent. At two weeks post immunization significant levels of pertussis toxin neutralizing antibody are not observed, but at 4 weeks, the neutralization titers increase with the greatest response seen at the 75 μg dose.

Both the ELISA response and neutralization titer in the CHO cell assay were found to be dose dependent, and subject to increase by administering a booster dose.

TABLE V

Pertussis toxin antibodies, determined by ELISA, of juvenile rhesus injected with pertussis toxoid (PTH-05) adsorbed.

| μg toxoid | n = | ELISA Units (Responders) | | | | | |
|---|---|---|---|---|---|---|---|
| | | Day 0 | Day 21 | Day 28 | Day 42 | Day 71 | Day 92 |
| 100 | 9 | 1.8 | 42 (7) | 95 (9) | 58 (9) | 29 (7) | 85 (9) |
| 50 | 9 | 2.2 | 29 (6) | 65 (9) | 27 (6) | 25 (8) | 59 (8) |
| 10 | 9 | 2.4 | 11 (3) | 28 (7) | 18 (6) | 20 (5) | 29 (7) |
| PBS | 3 | 2.3 | 2.3 (0) | 2.6 (0) | 3.3 (0) | 5.4 (0) | 2.8 (0) |

Juvenile rhesus were immunized with pertussis toxoid, PTH-05, adsorbed, on days

TABLE III

Pertussis toxin antibodies, as measured by ELISA, in mice immunized with pertussis toxoids, adsorbed, and US-8 Reference Cellular Pertussis Vaccine

| PTH-04 | | | PTH-05 | | | PTH-06 | | | US-8 Reference | | |
|---|---|---|---|---|---|---|---|---|---|---|---|
| (μg) | 2 wks | 4 wks | (μg) | 2 wks | 4 wks | (μg) | 2 wks | 4 wks | Dil. | 2 wks | 4 wks |
| 75 | 123 | 431 | 75 | 101 | 352 | 75[a] | 59 | 118 | 1/10 | 16 | 25 |
| 25 | 65 | 163 | 25 | 64 | 174 | 50[a] | 41 | 71 | 1/50 | 7 | 23 |
| 8 | 40 | 96 | 8 | 22 | 60 | 10[a] | 17 | 34 | 1/250 | 7 | 6 |
| 3 | 7 | 31 | 3 | 8 | 19 | 50[b] | 48 | 80 | PBS | 7 | 6 |
| PBS | 7 | 6 | PBS | 7 | 6 | 10[c] | 35 | 41 | | | |
| | | | | | | PBS | 8 | 4 | | | |

[a]Mice were immunized with bulk lot PTH-06-75.
[b]Mice were immunized with bulk lot PTH-06-50.
[c]Mice were immunized with bulk lot PTH-06-10.
Mice were injected intraperitoneally with 0.5 ml of either of the three pertussis toxoids, PTH-04, PTH-05 or PTH-06 or the U.S. Reference cellular pertussis vaccine, US-8. The mice were bled 2 or 4 weeks later and their pertussis toxin antibodies, measured by ELISA, are depicted as the mean.

TABLE IV

Serum neutralizing activity, as measured by CHO cell assay, of mice immunized with pertussis toxoids, adsorbed, and US-8 Reference Cellular Pertussis Vaccine (mean of 10–11 mice/group)

| PTH-04 | | | PTH-05 | | | TH-06* | | | US-8 Reference | | |
|---|---|---|---|---|---|---|---|---|---|---|---|
| (μg) | 2 wks | 4 wks | (μg) | 2 wks | 4 wks | (μg) | 2 wks | 4 wks | Dil. | 2 wks | 4 wks |
| 75 | <5 | 85 | 75 | <5 | 12 | 75[a] | <5 | 91 | 1/10 | <5 | <5 |
| 25 | <5 | 25 | 25 | <5 | <5 | 50[a] | <5 | 43 | 1/50 | <5 | <5 |
| 8 | <5 | 10 | 8 | <5 | 10 | 10[a] | <5 | 9.4 | 1/250 | <5 | <5 |
| 3 | <5 | <5 | 3 | <5 | <5 | 50[b] | <5 | 38 | PBS | <5 | <5 |
| PBS | <5 | <5 | PBS | <5 | <5 | 10[c] | <5 | 41 | | | |
| | | | | | | PBS | <5 | <5 | | | |

[a]Mice were immunized with bulk lot PTH-06-75.
[b]Mice were immunized with bulk lot PTH-06-50.
[c]Mice were immunized with bulk lot PTH-06-10.
Mice were injected intraperitoneally with 0.5 ml of either of the three pertussis toxoids, PTY-04, PTH,05 or PTH-06 or the U.S. Reference cellular pertussis vaccine, US-8. The mice were bled 2 or 4 weeks later and the neutralizing activity of their sera to pertussis toxin was measured by the CHO cell assay as described in the Methods Section.

Adsorbed pertussis toxoid was also shown to produce an immune response in rhesus monkeys (Table V and VI). Pertussis toxin specific antibody as measured by ELISA results in a response comparable to that seen in sera obtained from patients recovering from pertussis wherein using the same reference sera patients gave a mean ELISA response of 115. The immune response also resulted in the production of antibodies which were able to neutralize pertussis toxin in the CHO cell assay.

0, 21 and 71 with the indicated dose. The pertussis toxin antibodies of these samples are depicted as the geometric mean and the number of responders, designated as monkeys with a fourfold or greater rise over their pre-immunization level, are shown in the parenthesis.

TABLE VI

Pertussis toxin neutralization antibodies (CHO cell assay) of juvenile rhesus injected with pertussis toxoid (PTH-05), adsorbed.

| μg toxoid | n = | Reciprocal neutralization titer and (responders) | | | | | |
|---|---|---|---|---|---|---|---|
| | | Day 0 | Day 21 | Day 28 | Day 42 | Day 71 | Day 92 |
| 100 | 9 | <5 (9) | 16 (7) | 23 (9) | 44 (9) | 6 (4) | 20 (8) |
| 50 | 9 | <5 (0) | 7 (6) | 17 (9) | 22 (6) | <5 (0) | 10 (7) |
| 10 | 9 | <5 (0) | 12 (3) | 17 (7) | 14 (6) | 6 (3) | 9 (6) |
| PBS[a] | 2 | <5 (0) | <5 (0) | <5 (0) | <5 (0) | <5 (0) | <5 (0) |

[a]One rhesus was excluded from this group because an initial CHO cell titer of 10 was observed.
Juevnile rhesus were immunized with pertussis toxoid, PTH-05, adsorbed, on days 0, 21 and 71 with the indicated dose. The results are depicted as the geometric mean and the number of responders, designated as monkeys with neutralization titers equalto or greater than 10 (shown in the parenthesis).

POTENCY OF PERTUSSIS TOXOIDS

Pertussis toxoids were examined for their ability to protect mice against intra-cerebral challenge with *B*.

Figure 3:
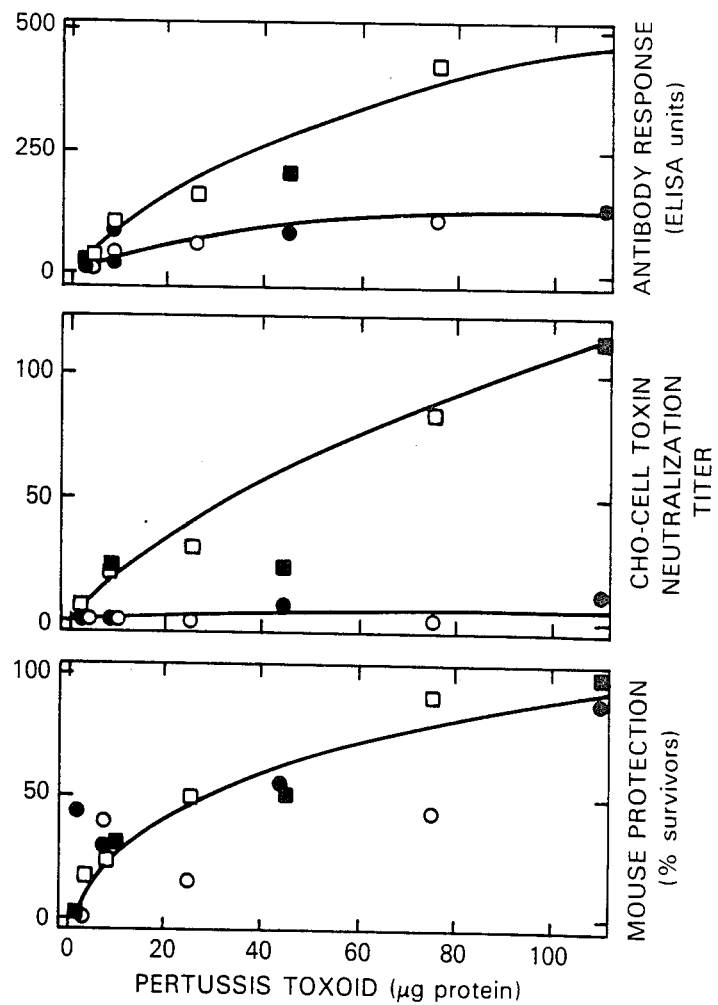
FIG. 3 shows the stability of pertussis toxoids.

*pertussis* organisms (Table VII, FIG. 3). With the three lots of pertussis toxoid vaccine tested, the ED-50 (μg protein) calculated at two weeks were: 44 μg for PTH-04 (the 8 μg data point was excluded), 51 μg for PTH-05, and 30 μg for PTH-06-75. While the pertussis toxoids exhibit the ability to protect mice against cerebral challenge, the potency is insufficient to comply with current regulations of the FDA. The adsorbed pertussis toxoids give less than 10 mouse protective units per mg protein. The proposed toxoid dose of between 10 and 75 μg will result in less than 0.4 mouse protective units per single human dose.

The potency of pertussis toxoid vaccines was assessed by challenging mice with a lethal dose of pertussis toxin (Table VIII). The amount of protein for the ED-50 was calculated to be: 5.2 μg for PTH-04, 41 μg for PTH-05, and 4.9 μg for PTH-06-50. The low potency of PTH-05 in this assay reflects the low potency of this lot of vaccine in eliciting neutralizing antibodies in the standard CHO-cell neutralization assay (Table IV).

TABLE VII

Protection against intracerebral challenge of mice with *Bordetella pertussis* conferred by pertussos toxoids, adsorbed, and U.S. 8 Reference Cellular Pertussis Vaccine (Survivors/Total).

| PTH-04 | | | PTH-05 | | | PTH-06 | | | US-8 Reference | | |
|---|---|---|---|---|---|---|---|---|---|---|---|
| (μg) | 2 wks | 4 wks | (μg) | 2 wks | 4 wks | (μg) | 2 wks | 4 wks | Dil. | 2 wks | 4 wks |
| 75 | 4/9 | 11/11 | 75 | 3/11 | 2/11 | 75[a] | 7/11 | 6/8 | 1/10 | 6/10 | 6/11 |
| 25 | 2/11 | 5/11 | 25 | 0/11 | 1/11 | 50[a] | 4/10 | 5/11 | 1/50 | 2/10 | 2/11 |
| 8 | 4/10 | 3/11 | 8 | 0/11 | 0/11 | 10[a] | 2/11 | 2/11 | 1/250 | 0/11 | 0/11 |
| 3 | 0/11 | 2/11 | 3 | 0/11 | 0/11 | 50[b] | 5/11 | 7/11 | PBS | 0/11 | 0/11 |
| PBS | 0/11 | 0/11 | PBS | 0/11 | 0/11 | 10[c] | 5/11 | 7/11 | | | |
| | | | | | | PBS | 0/11 | 0/10 | | | |

[a]Mice were immunized with bulk lot PTH-06-75.
[b]Mice were immunized with bulk lot PTH-06-50.
[c]Mice were immunized with bulk lot PTH-06-10.

Mice were injected intraperitoneally with 0.5 ml of either of the three pertussis toxoids, PTH-04, PTH-05 or PTH-06 or the U.S. Reference cellular pertussis vaccine, US-8 and then challenged 2 or 4 weeks later with *B. pertussis* organisms injected intracerebrally as described in the Methods Section. The survivors were recorded 14 days after the challenge as prescribed in the Code of Federal Regulations [111].

TABLE VIII

Protection in mice conferred by pertussis toxoids and U.S. Standard Pertussis Vaccine, US-8, against challenge pertussis toxin

| Dose injected | Survivors/total challenged | | | |
|---|---|---|---|---|
| (μg protein) | PTH-04 | PTH-05 | PTH-06-50 | US-8[a] |
| 50 | 10/12 | 8/10 | 9/10 | 0/10 |
| 10 | 10/12 | 0/10 | 9/10 | 0/10 |
| 2 | 0/12 | 0/10 | 0/10 | 0/10 |

TABLE VIII-continued

Protection in mice conferred by pertussis toxoids and U.S. Standard Pertussis Vaccine, US-8, against challenge pertussis toxin

| Dose injected | Survivors/total challenged | | | |
|---|---|---|---|---|
| (μg protein) | PTH-04 | PTH-05 | PTH-06-50 | US-8[a] |
| PBS | 0/12 | 0/10 | 0/10 | 0/10 |

[a]The US-8 Standard vaccine was administered at 0.05 μl, 0.01 μl or 0.002 μl with the doses of 50, 10 and 2 micrograms of the pertussis toxoids.

Mice were injected with 0.5 ml of each of the pertussis toxoids or dilutions of the U.S. Reference Pertussis Vaccine, US-8, and challenged with $5.2 \times LD_{50}$ dose of pertussis toxin for the mice injected with PTH-04 and with $15.4 \times LD_{50}$ for the mice injected with the PTH-05, PTH-06 and US-8. The $ED_{50}$ of PTH-04 was 5.2 micrograms, of PTH-05 was 41.0 micrograms and 4.9 micrograms for PTH-06.

THE EFFECT OF ACTIVE PERTUSSIS TOXIN

When mice are given a non-lethal, non-immunogenic dose of active pertussis toxin one hour prior to immunization with adsorbed pertussis toxoid, a marked change is seen in potency as judged by the mouse intra-cerebral challenge model (Table IX). Active pertussis toxin results in the decrease of the ED-50 from 51 μg to 12.5 μg. This increase in vaccine potency does not appear to result from enhanced immune response as judged by ELISA or CHO-cell neutralization titer. It should be noted that this is the test currently used to standardize whole cell pertussis vaccines. Since active pertussis toxin can potentially contribute to adverse reactions, the procedure employed here to produce acellular pertussis vaccine is designed to reduce active pertussis toxin to minimal levels.

TABLE IX

Effect of a sub-lethal, non-immunogenic dose of pertussis toxin (0.1 μg) injected concurrently with pertussis toxoid, PTH-05, on antitoxin levels and protection against intracerebral challenge of mice with *Bordetella pertussis*.

| | IC challenge (Live/total) | | | | ELISA | | | | CHO cell assay | | | |
|---|---|---|---|---|---|---|---|---|---|---|---|---|
| ug toxoid | toxin − | | toxin + | | toxin − | | toxin + | | toxin − | | toxin + | |
| injected | 2 wk | 4 wk | 2 wk | 4 wk | 2 wk | 4 wk | 2 wk | 4 wk | 2 wk | 4 wk | 2 wk | 4 wk |
| 75 | 3/11 | 2/11 | 9/11 | 8/11 | 101 ± 25 | 352 ± 173 | 80 ± 24 | 252 ± 80 | <5 | 12 | <5 | 12 |
| 25 | 0/11 | 1/11 | 5/10 | 5/11 | 64 ± 31 | 174 ± 72 | 44 ± 22 | 138 ± 92 | <5 | 4 | <5 | 4 |
| 8 | 0/11 | 0/11 | 3/11 | 4/11 | 22 ± 10 | 60 ± 27 | 36 ± 17 | 106 ± 50 | <5 | <5 | <5 | <5 |
| 3 | 0/11 | 0/11 | 1/10 | 7/11 | 8 ± 3 | 19 ± 11 | 27 ± 12 | 70 ± 20 | <5 | <5 | <5 | <5 |

Mice were immunized with PTH-05, adsorbed, alone or with 0.1 microgram of pertussis toxin injected intravenously one hour prior to immunization. The mice were bled for sera and, on the next day, injected intracerebrally with *B. pertussis* organisms as outlined in the text. The pertussis toxin antibodies determined by ELISA are presented as the mean ± standard deviation. The pertussis toxin antibodies determined by the CHO cell assay are presented as the geometric mean.

THE EFFECT OF ADJUVANT CONTENT ON POTENCY OF PERTUSSIS TOXOIDS

Pertussis toxoid Lot PTH-06 was monitored for potency by ELISA (Table III), CHO-cell neutralization titer (Table IV), and mouse potency (Table VII) after being compounded at different adjuvant/protein ratios (Table X). As judged by each of these criteria an increase in the ratio of aluminum to protein resulted in a more potent vaccine. The response elicited by 10 μg toxoid in lot PTH-06-10 is equivalent to the response seen with 50 μg toxoid in lot PTH-06-75.

TABLE X

Protein and aluminium content of pretoxoid and lots and PTH-06 sublots

| Lot | Protein (μg/mL) | Alhydrogel (mg Al+++/mL) |
| --- | --- | --- |
| PTH-04 | 190 | 0.95 |
| PTH-05 | 140 | 0.75 |
| PTH-06-75 | 150 | 1.0 |
| PTH-06-50 | 100 | 1.0 |
| PTH-06-10 | 20 | 1.0 |

The toxoids were adsorbed to the Alhydrogel for 48 hours at 4° C. with gentle agitation. The bottle of PTH-06 bulk toxoid were then transferred to Pharmacy Section, CC, NIH for delivery into 5.0 mL vials to contain 2.2 ml each.

STABILITY AND TOXICITY OF ADSORBED PERTUSSIS TOXOIDS

Adsorbed pertussis toxoids have been stored at 4° C. for periods of up to six months with no apparent change in potency (FIG. 3), as judged by ELISA, induction of pertussis toxin neutralizing antibodies in the CHO cell assay, and mouse protection. When adsorbed pertussis toxoid was injected intraperitoneally no toxicity was observed, as judged by white blood count and sensitization to histamine, when mice were observed for up to 3 weeks following injection (Table XI). Storage of non-adsorbed pertussis toxoids for more than 3 weeks at 37° C. does not lead to reversion to active toxin as measured by ADP-ribosylation of transducin (Table XII).

TABLE XI

Lymphocytosis-promoting and histamine-sensitizing activity of pertussis toxoid, adsorbed, Lot PTH-05.

| | White blood cell count | | | Histamine challenge (survivors/total) | | | |
| --- | --- | --- | --- | --- | --- | --- | --- |
| DPI[a] | P. toxin | Alhydrogel | PTH-05 | DPC[b] | P. toxin | Alhydrogel | PTH-05 |
| 3 | 34,200 | 4,300 | 3,400 | 4 | 0/5 | 5/5 | 5/5 |
| 7 | 23,600 | 4,300 | 5,600 | 8 | 0/4 | 5/5 | 5/5 |
| 14 | 9,600 | 3,300 | 5,700 | 15 | 0/5 | 4/5 | 4/5 |
| 21 | 4,100 | 4,000 | 3,900 | 22 | 0/4 | 3/5 | 3/5 |

*DPI — Days post immunization
+DPC — Days post challenge
Groups of fives mice were injected intraperitoneally with either 1.0 ml of PTH-05, 1.0 ml of PBS containing 0.75 mg of aluminium as Alhydrogel, or 1.0 ml of PBS containing pertussis toxin. Mice were bled on days 3,7,14 and 21 after imunization and their mean WBC listed. The following day, the mice were injected intraperitoneally with 10 μl/gram body of histamine hydrochloride, a ten fold higher dose than specified. The survivors of each group of five mice is shown.

TABLE XII

Transducin ADP-ribosylation activity in pertussis toxoid preparations stored at 37 C. for extended periods.

| Days at 37 C. | ADP-ribosylation Activity (Units per ml) | |
| --- | --- | --- |
| | PTH-04 | PTH-05 |
| 0 | <30 | 270 |
| 8 | <30 | <30 |
| 14 | <30 | 52 |
| 25 | <30 | 37 |

Preparations of hydrogen peroxide inactivated pertussis toxin were stored for the indicated number of days and then assayed for ADP-ribosyltransferase activity with transducin as the acceptor. Data are expressed as nanograms of toxin per ml calculated on the basis of a reference pertussis toxin preparation.

It is clear from the data presented herein that treatment of petussis toxin with hydrogen peroxide as described supra, yields chemically irreversible antigen which is safe (non-toxic) without adverse effects commonly encountered in prior art preparations. Furthermore, the preparation is stable, immunogenic and protective against pertussis infection. Of course, the novel method illustrated herein by the specific example of pertussis toxin is not limited to pertussis toxin only. It is of general application and can be similarly used for the preparation of other toxins such as tetanus, diptheria, cholera toxins and the like.

It is apparent, of course, that the toxin of the present invention can also be used in a pharmaceutical composition comprising immunogenic amount of the toxoid and a pharmaceutically acceptable carrier such as sterile, physiological saline, non-toxic physiological buffers and the like well known in the art. Of course, sterilants, additives and adjuvants, such as aluminum compounds and the like well known in the art can also be present in such preparations.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A method of preparing toxoid comprising treating at least partially isolated protein toxin with an amount of an oxidant and trace amount of a metal ion to chemically inactivate said toxin while retaining immunogenic property of said toxin and thereafter recovering the inactivated toxin or parts thereof, wherein said oxidant oxidizes said toxin at specific positions in peptide chain of the toxin where amino acid residues selected from the group consisting of cysteine, cystine, methionine, tryptophan and tyrosine occur.

2. The method of claim 1 wherein said oxidant is selected from the group consisting of hydrogen peroxide, sodium peroxide, N-chloro-4-methyl-benzenesulfonamide sodium salt (chloramine-T), performic acid, dioxaneperoxide, periodic acid, Na-permanganate, sodium hypochlorite and mixture thereof.

3. The method of claim 2 wherein said oxidant is hydrogen peroxide.

4. The method of claim 2 wherein said oxidant is chloramine-T.

5. The method of claim 1 wherein said metal ion is selected from the group consisting of ferrous, ferric, cobalt and chromium.

6. The method of claim 1 regulating rate of chemical inactivation of the toxin, caused by the metal ion and the oxidant, by addition of a chelating agent.

7. The method of claim 6 wherein said chelating agent is ethylenediaminetetraacetate.

8. The method of claim 1 wherein said toxin is a bacterial toxin.

9. The method of claim 8 wherein said toxin is pertussis toxin.

10. A toxoid prepared by the method of claim 1.

11. The toxoid of claim 10 being adjuvanted with an aluminum compound.

12. The toxoid of claim 11 being cryopreserved.

13. The toxoid of claim 10 capable of inducing protective antibodies in a host when said toxoid is administered to immunogenic amount to said host.

14. The toxoid of claim 13 wherein said toxoid is pertussis toxid.

15. A pharmaceutical composition comprising immunogenic amount of the toxoid of claim 10 and a pharmaceutically acceptable carrier.

16. The pharmaceutical composition of claim 15 wherein said toxoid is pertussis toxoid.

17. The pharmaceutical composition of claim 16 wherein said toxoid is adjuvanted with an aluminum salt.

18. A method of inducing protective immunity against *Bordetelle pertussis* in a susceptible host comprising administering to susceptible host immunogenic amount of pertussis toxoid prepared by the method of claim 1.

* * * * *